United States Patent [19]

Zaromb

[11] Patent Number: 5,328,851
[45] Date of Patent: Jul. 12, 1994

[54] HIGH-THROUGHPUT LIQUID-ABSORPTION PRECONCENTRATOR SAMPLING METHODS

[76] Inventor: Solomon Zaromb, 95706 William Dr., Hinsdale, Ill. 60521

[21] Appl. No.: 993,080

[22] Filed: Dec. 18, 1992

Related U.S. Application Data

[60] Division of Ser. No. 499,602, Mar. 26, 1990, Pat. No. 5,173,264, which is a continuation-in-part of Ser. No. 330,654, Mar. 30, 1989, Pat. No. 4,912,051, and a continuation-in-part of Ser. No. 330,655, Mar. 30, 1989, Pat. No. 4,977,095.

[51] Int. Cl.$^5$ .................. G01N 1/18; G01N 35/08
[52] U.S. Cl. ........................ 436/178; 436/52; 436/168; 436/172; 472/52; 472/88; 472/69; 472/91; 261/95; 261/99; 261/104
[58] Field of Search ................ 436/52-55, 436/161, 167, 168, 169, 171, 172, 178; 422/52, 56, 88, 89, 69, 98, 91; 95/211; 261/95, 99, 104

[56] References Cited

U.S. PATENT DOCUMENTS

| | | | |
|---|---|---|---|
| 2,431,455 | 11/1947 | Blanding | 95/211 X |
| 3,404,512 | 10/1968 | Tomany | 95/211 X |
| 3,409,279 | 11/1968 | Metrailer | 95/211 X |
| 4,533,367 | 8/1985 | Hadzismajlovic | 95/211 |
| 4,549,965 | 10/1985 | Davis | 436/161 |
| 4,954,318 | 9/1990 | Yasuto et al. | 436/167 X |

OTHER PUBLICATIONS

Siemer et al., "Silicone Rubber Tubing for Elimination of Background Cond. in Anion Chrom.", Anal. Chem. vol. 56, pp. 1033-1034 1984.
Siemer et al., "Carbon Dioxide Permeable Tubing for Post-Suppression in Ion Chrom.", Anal. Chem. vol. 56, pp. 1085-1089, 1984.
Tanner et al., "Sampling and Det. of Gas Phox H$_2$O$_2$ Following Removal of O$_3$ by Gas-Phase Reaction with Nitro Oxide", Anal. Chem., 58, 1858-1865, 1986.
Zaromb et al., "Technique for Calibrating Air Samples and Certain Other Anal. Devices", J. of Chromatography, 438, pp. 100-102, 1988.
Zaromb et al., "Simple Permeation Absorber for Sampling and Preconcentrating Hazardous Air Contaminants", J. of Chromatography, 439, pp. 283-299, 1988.
Zaromb, "Preconcentrating Air Samples-PAS-100", Tech. Notes p. 612 (NTIS, Jul. 1988).
Kandallu, "An Evaluation of a Permeable-Absorption Type Preconcentrator Sampler in the Measurement of Low Conc. of Hydrazine", 1988.

*Primary Examiner*—James C. Housel
*Assistant Examiner*—Milton I. Cano

[57] ABSTRACT

A system for detecting trace concentrations of an analyte in air includes a preconcentrator for the analyte and an analyte detector. The preconcentrator includes an elongated tubular container comprising a wettable material. The wettable material is continuously wetted with an analyte-sorbing liquid which flows from one part of the container to a lower end. Sampled air flows through the container in contact with the wetted material with a swirling motion which results in efficient transfer of analyte vapors or aerosol particles to the sorbing liquid and preconcentration of traces of analyte in the liquid. The preconcentrated traces of analyte may be either detected within the container or removed therefrom for injection into a separate detection means or for subsequent analysis.

19 Claims, 7 Drawing Sheets

HIGH-THROUGHPUT LIQUID-ABSORPTION PRECONCENTRATOR SAMPLING METHODS

CONTRACTUAL ORIGIN OF THE INVENTION

The United States Government has rights in this invention pursuant to Contract No. W-31-109-ENG-38 between the U.S. Department of Energy and The University of Chicago representing Argonne National Laboratory.

REFERENCE TO RELATED APPLICATIONS

This is a divisional application of application Ser. No. 499,602, filed Mar. 26, 1990, now U.S. Pat. No. 5,173,264, which is a continuation-in-part of copending U.S. applications Ser. No. 330,654, filed Mar. 30, 1989, entitled "Method for Preconcentrating a Sample for Subsequent Analysis", now U.S. Pat. No. 4,912,051 and Ser. No. 330,655, filed Mar. 30, 1989, entitled "Liquid Absorption Preconcentrator Sampling Instrument", now U.S. Pat. No. 4,977,095, the disclosures of which are incorporated herein by reference.

BACKGROUND OF THE INVENTION

The present invention relates to analytical instruments for detecting and identifying trace levels of selected vapors, and in particular to portable instruments. The present invention has particular application to rapid detection and identification of trace air contaminants such as cocaine or heroin.

It is known to preconcentrate analytes in air samples by the use of sorbents, and thereby increase the sensitivity of detecting instruments. The aforementioned copending U.S. application Ser. No. 330,654 discloses the use of an absorption preconcentrating air sampler to increase the sensitivity of an analytical instrument. In such a sampler, a substantial portion of the analyte contained in a large volume of air becomes absorbed in a small volume of liquid extractant that can be injected directly into an analytical instrument, such as a liquid chromatograph. As compared with other methods, the direct absorption of an analyte from an arbitrarily large volume of air into a small volume of liquid extractant offers the advantages of low-temperature operation, simplicity, speed and flexibility. That device has proved effective for detecting hazardous analytes, such as highly carcinogenic primarily aromatic amines, when used with gas or liquid chromatographs.

Liquid-absorption sampling has been used successfully for the collection of many different analytes, including trinitrotoluene, alkaloids, primary aromatic amines, hydrazines, hydrogen peroxide, nitrogen oxide, diisocyanates, 2-chloronitrobenzene, and several inorganic halogen compounds (HCl, HF, $F_2$, and other hydrolyzable fluorides). Preferably, as disclosed in copending application Ser. No. 330,654, the extractant should react rapidly with the analyte to yield a light-absorbing or light-emitting product that can be measured colorimetrically or by chemiluminescence using a built-in, preferably fiber-optic, detector. This would yield a portable yet highly sensitive, near real-time, self-contained analytical instrument. Alternatively, near real-time recording of sampled air compositions can be obtained by feeding the collected liquid into separate properly marked vials at predetermined intervals.

It is also recognized that many chemical compounds tend to be preferentially adsorbed onto solid surfaces, especially air-borne solid particulates, or absorbed by liquids, especially water droplets. This is true of most explosives and at least some propellants and chemical warfare agents. Therefore, suspended liquid and solid particulates may serve as natural preconcentrators. It would be advantageous to collect analytes from airborne water droplets and/or particulates. This advantage is not readily offered by alternative types of preconcentrators.

Copending U.S. application Ser. No. 330,655 provides for the applicability of the absorption preconcentrating sampler of the aforementioned copending U.S. application Ser. No. 330,654 by coupling it with other types of analytical techniques to effect detection of a wide variety of analytes. A further advanced high-throughput liquid-absorption preconcentrator (HTLAP) is herein disclosed which incorporates the preconcentrating sampler of copending U.S. application Ser. No. 330,655 and the analytical system of copending U.S. application Ser. No. 330,654, and which further provides for rapid detection and analysis of trace air contaminants.

SUMMARY OF THE INVENTION

It is a general object of the present invention to extend the applicability of the HTLAP to the collection of aerosol-borne analytes to further enhance the sensitivity and efficiency of the resulting preconcentrator-analyzer system.

An important feature of the invention is a smaller collection volume of liquid extractant which facilitates interfacing with commercially available instruments and allows use of most of the collected sample in a single analysis. This, in turn, greatly enhances the sensitivity of measurements and permits specification of detection capabilities in terms of the weight of collected analyte rather than in terms of its concentration in the liquid extractant.

In connection with the foregoing features, it is another feature of the invention to provide a system of the type set forth, which offers the advantages of low-temperature operation, selectivity, simplicity, speed, and ready adjustability to a wide dynamic range of analyte concentrations. Since it requires no thermal desorption, it is especially suited for highly reactive and thermally labile compounds. The invention can also be made highly selective to analytes of interest by proper choice of the liquid extractant.

Yet another feature of the invention is a transportable unit which collects liquid samples over fixed time intervals, with interruptions between sampling periods being effected manually. Automatic collection of a multiplicity of liquid samples over short time intervals (for near-real time determinations of the compositions of the sampled air) are also possible.

These and other features of the invention are attained by providing a system for detecting traces of an analyte in a fluid medium comprising: an elongated gas impermeable container having a longitudinal wall, an upper end and a lower end, and wettable material disposed in the container and extending through much of the length thereof, means for continuously wetting the wettable material with an analyte-sorbing liquid so that the liquid moves toward one end of the material for wetting much of the length thereof, means for flowing the gaseous medium through an inlet opening in the container in contact with the wettable material for trapping and preconcentrating traces of analyte in the sorbing liquid, and means for removing from the container the sorbing liquid containing the preconcentrated traces of analytes. To prevent losses of analyte by adsorption onto solid surfaces, any dry surfaces within the apparatus that the gaseous medium may encounter before coming into contact with the liquid either have a negligibly small area or are maintained at a temperature at which adsorption of analyte is negligibly low.

Additional objects, advantages and novel features of the invention will be set forth in part in the description which follows, and in part will become apparent to those skilled in the art upon examination of the following drawings or may be learned by practicing the invention. The objects and advantages of the invention may be realized and attained by means of the instrumentalities and combinations particularly pointed out in the appended claims.

BRIEF DESCRIPTION OF THE DRAWINGS

For the purpose of facilitating an understanding of the invention there are illustrated in the accompanying drawings preferred embodiments thereof, from an inspection of which, when considered in connection with the following description, the invention, its construction and operation, and many of its advantages should be readily understood and appreciated.

DESCRIPTION OF THE PREFERRED EMBODIMENTS

Figure 1:
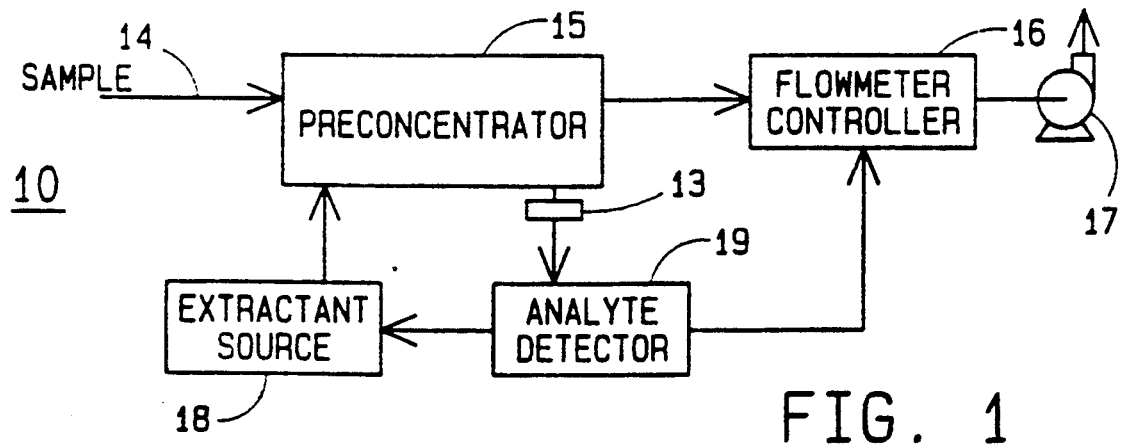
FIG. 1 is a functional block diagram illustrating an analytical system using a preconcentrator in accordance with the present invention.

Referring to FIG. 1, there is illustrated a generalized analytical system 10 in accordance with the principles of the present invention. The system 10 includes a preconcentrator 15, which may be of the type disclosed in the aforementioned copending U.S. application Ser. No. 330,655. The preconcentrator 15 has a fluid inlet 14 and a fluid outlet which is coupled through a flowmeter controller 16 to a pump 17. The system 10 also includes an extractant source 18 which is coupled to the preconcentrator 15 and provides analyte-sorbing liquid thereto. Also coupled to the preconcentrator 15 is an analyte detector 19, which may include an electrochemical, piezoelectric or immuno-assay detector. The output signal from the analyte detector 19 may be coupled to the extractant source 18 and to the flowmeter controller 16.

In operation, the fluid medium to be sampled, which contains traces of the analyte of interest, is drawn in through the inlet 14 into the preconcentrator 15, flowing outwardly through the flowmeter controller 16 and pump 17. The analyte-sorbing liquid, which is selected to preferentially absorb the analyte of interest, is injected from the extractant source 18 into on end of the preconcentrator 15 in which it absorbs traces of the analyte of interest in the sample medium flowing through the container. The analyte-enriched sorbing liquid then passes to the analyte detector 19, which produces a signal indicative of the presence of the analyte of interest.

Figures 2, 3:
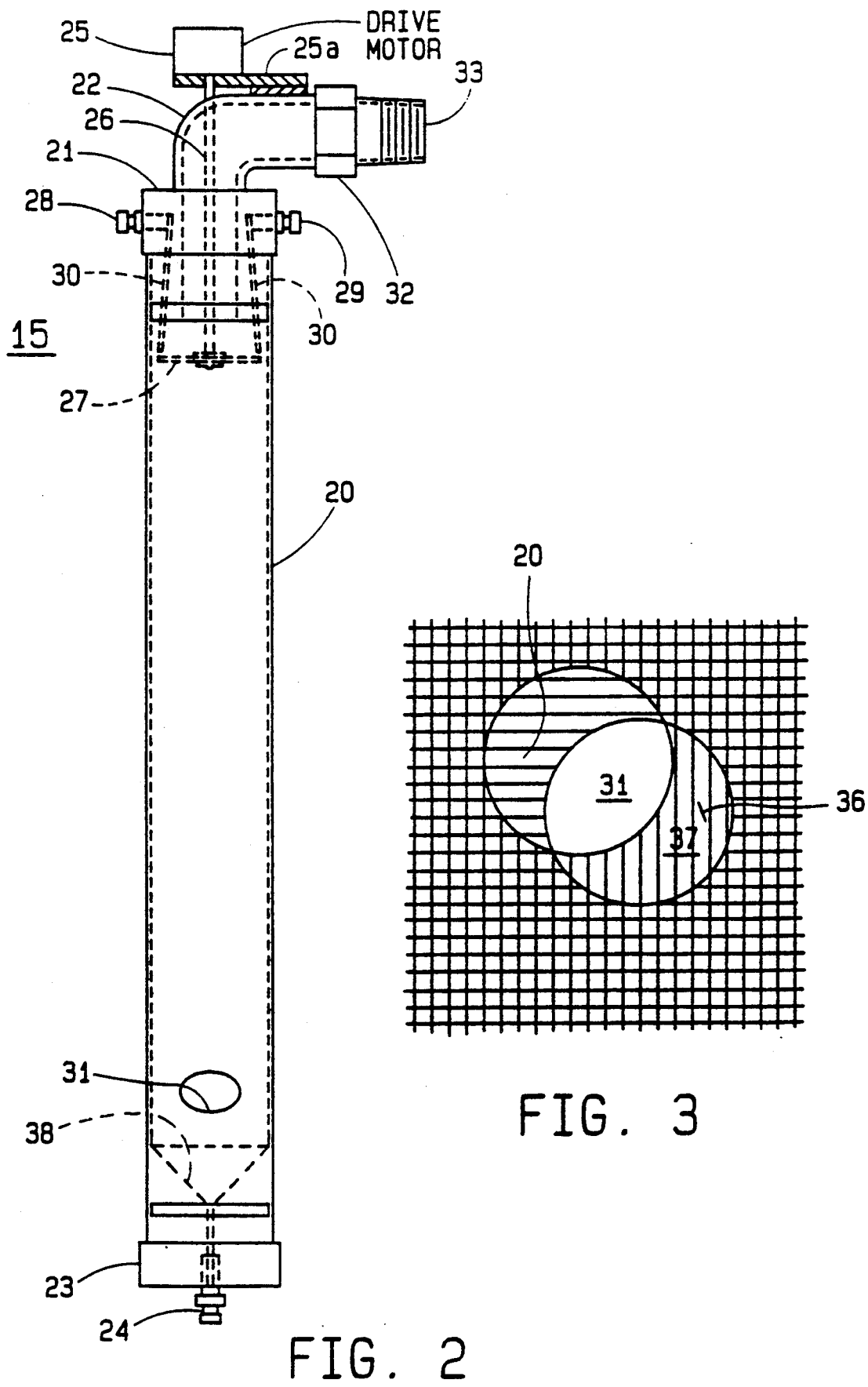
FIG. 2 is a side elevational view of a preconcentrator sampler for use in the system of FIG. 1.
FIG. 3 is an enlarged elevational view of an inlet hole of the preconcentrator of FIG. 2.

More specifically, and referring to FIG. 2, the preconcentrator sampler 15 includes an elongated tubular container 20, which is preferably circularly cylindrical in shape with its longitudinal axis disposed substantially vertically, and is formed of a suitable gas-impermeable material. Coupled to the container 20 at its upper end is a cylindrical coupling ring 21. Coupled to the coupling ring 21 is an elbow tube 22, one leg of which extends downwardly through the coupling ring 21 and into the upper end of the tubular container 20, coaxially therewith, and the other leg of which projects laterally outwardly therefrom substantially normal thereto. The coupling ring 21 provides a substantially air-tight coupling between the tubular container 20 and the outer surface of the elbow tube 22. The lower end of the container 20 is closed with an end cap 23 provided with an outlet port 24.

A drive motor 25 is mounted on a suitable support 25a on top of the elbow tube 22, the motor 25 having an output shaft 26 which extends through a complementary opening into the elbow tube 22 and downwardly through the vertical leg thereof, substantially coaxially therewith, being coupled at its lower end to the hub of a distributor wheel 27, which has a spoked configuration and an outer circumference slightly less than the inner circumference of the tubular container 20. Formed at diametrically spaced-apart locations in the coupling ring 21 are two liquid extractant entry ports 28 and 29, respectively communicating at their inner ends with two depending drip tubes 30, the lower ends of which respectively terminate a slight distance above the outer peripheral portion of the distributor wheel 27. It will be appreciated that, in use, the fitting 32 is adapted for coupling to the air pump 17 in FIG. 1 or to a conduit leading thereto.

Formed in the side wall of the tubular container 20 adjacent to the lower end thereof is an air inlet hole 31, which is preferably cut at a sharp angle, but not perpendicular to the wall of the container 20, so as to impact a tangential component, and hence turbulence, to the motion of the inrushing air. The flow dynamics and collection efficiency of the preconcentrator are greatly influenced by the size and geometry of the air inlet. Referring to FIG. 3, to assure that the entering air follows a swirling path (which results in swirling of the extractant, full wetting of the inner walls of the preconcentrator, and efficient analyte transfer from the air to the extractant), a 0.08-cm thick sheet of plastic 36, such as Teflon, having a 2.7-cm diameter hole 37 is taped over the air inlet hole 31 so that the holes 31 and 37 partly overlap to form a crescent-like circular or elliptical opening.

The tubular container 20 is made of a wettable material such as glass, preferably borosilicate glass having an interior diameter of about 60 mm. The term "wettable" as used herein, describes a material, on the surface of which a liquid will form a continuous liquid film, as opposed to beading up. For example, most plastics are not wettable because liquids tend to bead up on the surface thereof. Clean glass, however, can be wetted by certain liquids, such as aqueous solutions.

To facilitate collection of the liquid extractant, a conical cavity 38 is machined in the lower end of the container 20, in which the liquid flows and collects.

In operation, the air to be sampled is pulled into the tubular container 20 through the air inlet port 31 and flows upwardly through the tubular container 20 and out through the elbow tube 22 to the associated pump 17. The fact that the air stream enters and leaves the tubular container 20 in directions substantially normal to the longitudinal axis thereof, together with the relatively high velocity of the air flow, contributes to a turbulent flow of the air through the tubular container 20. Analyte-sorbing liquid is fed by gravity or by a metering pump (not shown) from the extractant source 18 through the inlet ports 28 and 29, and thence flows down through the drip tubes 30 onto the distributor wheel 27. The distributor wheel 27 is rotated by the drive motor 25 so that, as the liquid extractant is dripped thereonto, the extractant is thrown outwardly by centrifugal force onto the inner surface of the container 20. The liquid extractant then slowly moves down the wettable surface, aided by gravitational forces, along the length of the container 20 while wetting substantially the entire inner surface thereof. As the air sample flows upwardly through the tubular container 20 it contacts the wetted inner surface, and the analyte in the air is selectively absorbed by the analyte-sorbing liquid, and thereby preconcentrated. The analyte-enriched sorbing liquid then flows from the tubular container 20 into the conical cavity 38, where it may either be retained for the duration of a sampling period or caused to escape through the outlet port 24, from which it is removed for injection into the analyte detector 19.

Figure 11:
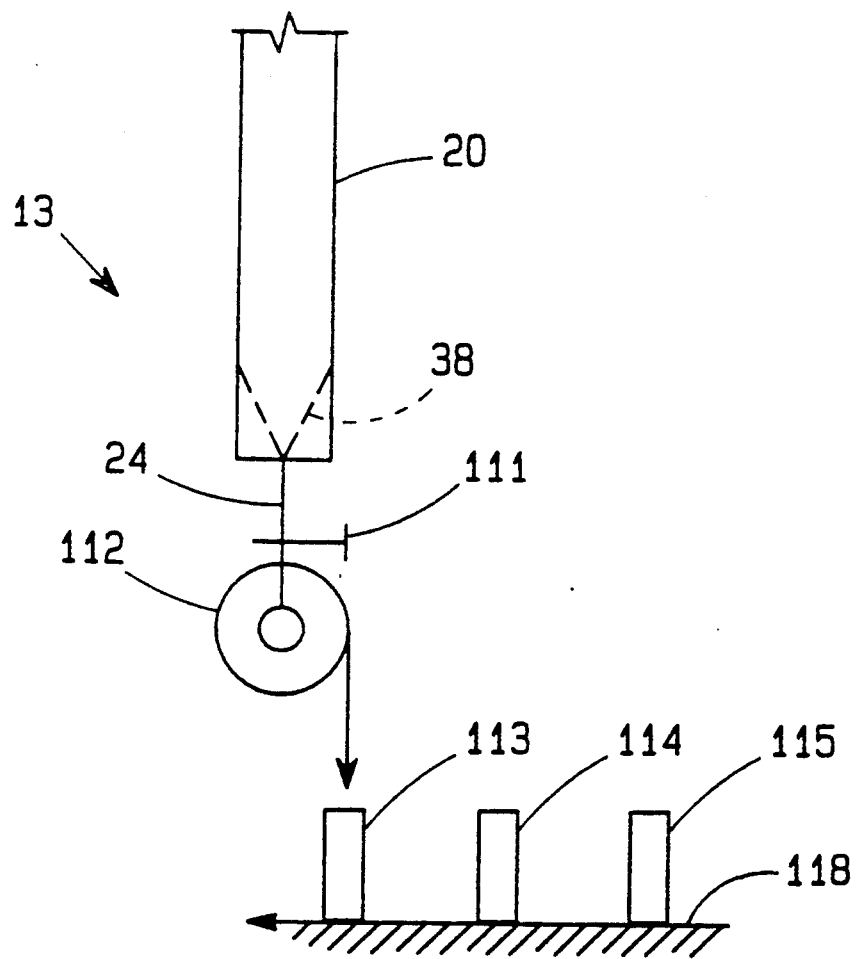
FIG. 11 shows a schematic diagram of a system for removing the collection of analyte-enriched sorbing liquid.

The collection of the analyte-enriched sorbing liquid can be effect by a removal means 13 which is shown schematically in FIG. 11. Removal means 13 comprises an electrically actuated valve 111 and a liquid metering pump 112, and may also comprise a moving belt or alternative support 118, all of which are controlled by a microprocessor-controller (45 in FIG. 4). To collect a single liquid sample over a relatively long time interval, e.g. 10-60 minutes for ultra-sensitive analyte detection, valve 111 is kept closed, so that the liquid sorbent accumulates in the cavity 38 and evaporates partly therein, thereby yielding a preconcentrated sample of analyte in a small volume of liquid (1-4 mL). At the end of the sampling period, valve 111 is opened and pump 112 draws the preconcentrated liquid from cavity 38 and transfers the liquid into either a collection vial 113 or into analyte detector 19. To collect multiple consecutive liquid samples for continuous near real-time monitoring of the compositions of the sampled air, the time intervals between successive collections can be shortened, e.g. to between 6 seconds and 10 minutes, with separate samples being introduced into a multiplicity of separate vials 113, 114, 115, each of which can be properly tagged and correlated with the sampling time interval by the microprocessor controller.

To assure wetting of the interior wall of the container 20, an ionizable or otherwise long-chain hydrocarbon detergent solution is included in the extractant, such as sodium-dodecyl sulfate, or cetyl-trimethyl ammonium bromide. The use of such a detergent permits a reduction in the extractant flow rate. Preferably, surfactants of the Triton series having the general formula $(CH_3)CCH_2C(CH_3)_2$—$C_6H_4$—$(OCH_2CH_2)_nOH$, where the alkane chains are attached to the benzene molecule in the para position and the average value of n is 9.5 for Triton X-100, or 7.5 for Triton X-114, manufactured by Rohm and Haas Company, as discussed in *Environmental Science and Technology*, Vol. 23, No. 7 (1989) at page 833, are used as the wetting agent in a concentration of about 0.1 gram per liter of water. This wetting agent results in an extractant flow rate in the container of about 1.0 mL/min, while still maintaining acceptable wetting of the interior wall of the container.

To maximize preconcentration of the analyte, it is desirable to minimize the volume of sorbing liquid collected at the outlet port 24. This minimization can be achieved by allowing the sorbing liquid to collect in the conical cavity for a desired period of time, for example 10-60 minutes. While the liquid collects, it partially evaporates and thereby reduces the volume collected at the outlet port 24.

In a constructional model of the preconcentrator sampler 15, the tubular container 20 has a length of about 24 inches and an inner diameter of about 2.5 inches. Air is pumped through the tubular container 20 at a rate of about 0.7 cubic meters per minute, in a swirling, highly turbulent motion, which assures rapid transfer of trace analytes to the liquid film which covers the interior surface of the container 20.

In the disclosed embodiment of the preconcentrator sampler 15, to assure that most of the analyte molecules are picked up by the extractant rather than being absorbed at solid surfaces, the total wetted surface area that is exposed to the sampled air, especially in the vicinity of inlet 31, should be several times greater than that of any dry surfaces within the container that may be exposed to the sampled air. Moreover, any dry surfaces within the apparatus 15 that the gaseous medium may encounter prior to coming into contact with the liquid should have either a negligibly small area or be maintained at a temperature at which adsorption of the analyte is negligibly low, preferably at least 50° C.

If the output signal from the analyte detector 19 is too small, the frequency with which analyte-sorbing liquid is withdrawn from the preconcentrator 15 may be decreased, thereby increasing its residence time in the preconcentrator 15 and/or the flowmeter controller 16 may be activated to increase the speed of the pump 17, thereby increasing the rate of flow of sample medium through the preconcentrator 15 to accordingly increase the volume of medium sampled per unit time period. On the other hand, if the output signal from the analyte detector 19 is too large, the frequency of withdrawal of the analyte-sorbing liquid from the extractant source 18 may be increased and/or, the pump 17 may be slowed.

Figure 4:
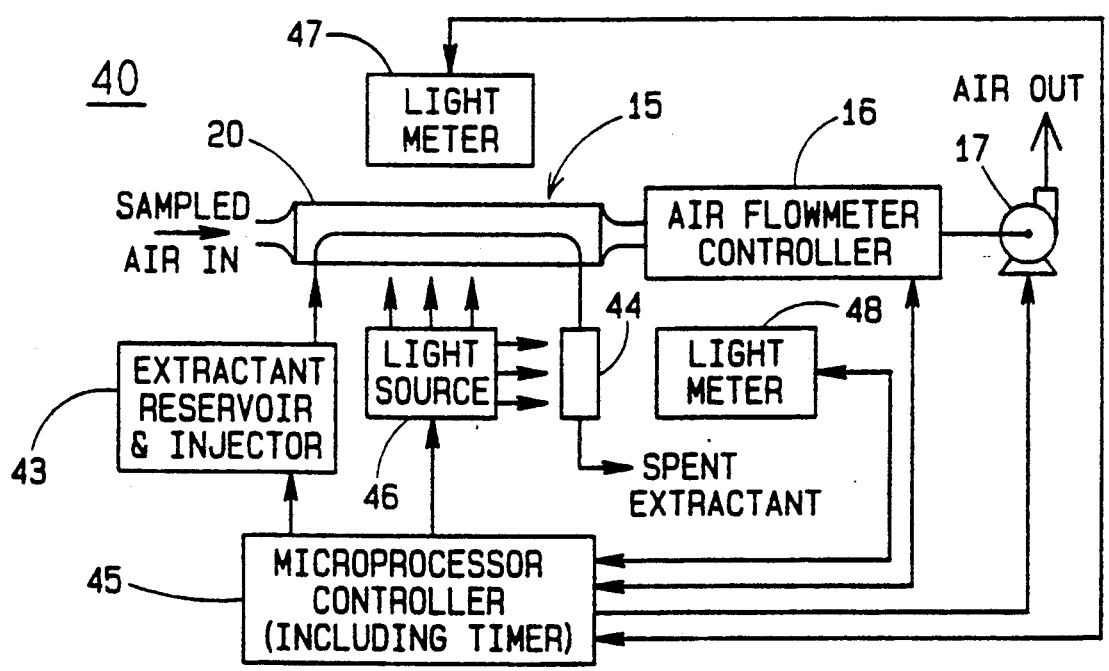
FIG. 4 is a functional block diagram of an analytical system constructed in accordance with one embodiment of the present invention utilizing colorimetric detection.

While the analyte detector 19 may be a separate and discrete detection unit, such as a chromatograph or a mass spectrometer, the present invention is particularly advantageous when used with an analyte detector which may be self-contained with the preconcentrator 15 in a portable or readily transportable system. Referring to FIG. 4, there is shown schematically an analytical system 40 in accordance with the present invention, which utilizes photometric analyte detection and, in particular, colorimetric detection. The system 40 includes the preconcentrator 15, which has a gas-impermeable elongated tubular container 20. The sampled gaseous medium, typically air, is drawn in through the air inlet of the container 20, and flows out through the air outlet and the air flowmeter controller 16 to the pump 17. An extractant reservoir and injector 43 is coupled to the liquid inlet of the container 20 and the outlet thereof is coupled through a collection vessel 44 to a spent extractant reservoir.

The system 40 includes a microprocessor controller 45 which includes a suitable timer. The microprocessor controller 45 is coupled to the flowmeter controller 16 for receiving output signals therefrom and for transmitting control signals thereto. The microprocessor controller 45 also has an output coupled to the pump 17, and has another output coupled to the extractant reservoir and injector 43 and another coupled to a light source 46. Preferably, the container 20 of the preconcentrator 15, especially at the conical cavity 38, and the collection vessel 44 are transparent or translucent to the light emitted from the light source 46. Light from the source 46 is transmitted through the preconcentrator 15 and the collection vessel 44 to light meters 47 and 48, respectively. The microprocessor controller 45 is coupled to the light meters 47 and 48 for receiving output signals therefrom and transmitting control signals thereto. The light meters 47 and 48 include light filters (not shown) having transmission bands which match the absorption band of the color that is generated by a selected colorimetric reagent in the presence of a selected analyte.

In operation, the air to be sampled is drawn through the preconcentrator 15 in the same manner described above with respect to FIG. 1. The reservoir and injector 43 continuously injects into the container 20 of the preconcentrator 15 a combination of analyte-sorbing liquid and reagent tailored to the analyte of interest. More specifically, the sorbing liquid is designed to preferentially absorb the analyte, while the reagent is responsive to the analyte to produce a chemical reaction which results in a predetermined color change. Thus, as the analyte is absorbed in the sorbing liquid in the container 20, it reacts with the reagent to produce the desired color change, which is made visible by illumination of the inner container 20 and the contents thereof by the light source 46. The color change is detected by the light meter 47, which may serve to provide a "coarse" measurement of the color change.

If a color change is detected by the light meter 47, the sample may be transferred from the container 20 to the collection vessel 44, in which it is again illuminated by the light source 46, the color change being detected by the light meter 48, which provides a more accurate reading of the amount of color change. This transfer is controlled by the microprocessor controller 45 in response to an output signal from the light meter 47.

In an alternative mode of operation, the light meter 47 may be dispensed with, and the reservoir and injector 43 may be controlled by the microprocessor controller 45 to continuously inject sorbent/reagent into the container 20 at a predetermined flow rate. After predetermined time intervals which are selected to be sufficiently long to permit a measurable amount of the analyte to be absorbed into the sorbing liquid, the analyte-enriched volume of sorbent is passed into the collection vessel 44, and the analyte therein is detected by the light meter 48. The microprocessor controller 45 may measure the difference between the output signals from the light meter 48 in response to consecutive volumes of sorbent.

As was explained above in connection with FIG. 1, if the output signal from the light meter 48 is too small, the microprocessor controller 45 operates to decrease the frequency of sorbent withdrawals and/or increase the speed of the pump 17. On the other hand, if the output signals form the light meter 48 are too high, the microprocessor controller 45 operates to increase the frequency of sorbent withdrawals and/or to decrease the speed of the pump 17.

More than seventy selective color indicating reactions are used in commercially available color detector tubes for a large number of compounds, including acrylinitrile, aniline, arsine, benzene, ethylene oxide, formaldehyde, hydrazine, mercury vapor, phosgene, phosphine, and vinyl chloride. Although designed for color detector tubes, these or similar reactions may also be utilized with the preconcentrator 15. When used in the system 40, these color indicating reactions provide much higher sensitivity than color detector tubes, resulting from the use of a smaller volume of extractant (typically about 0.1 ml, as compared with 1 g in color detector tubes), and arbitrarily high air volumes. Furthermore, the system 40 affords a much wider measurable concentration range than color detector tubes, achievable by measuring the air volume (or sample flow time) required to yield an observable or measurable color change. The system 40 also affords convenience and flexibility, since it is readily adapted to frequent repetitive measurements or quasi-continuous monitoring by automatically withdrawing the sorbing liquid either at predetermined time intervals or after a pronounced color change.

Figure 5:
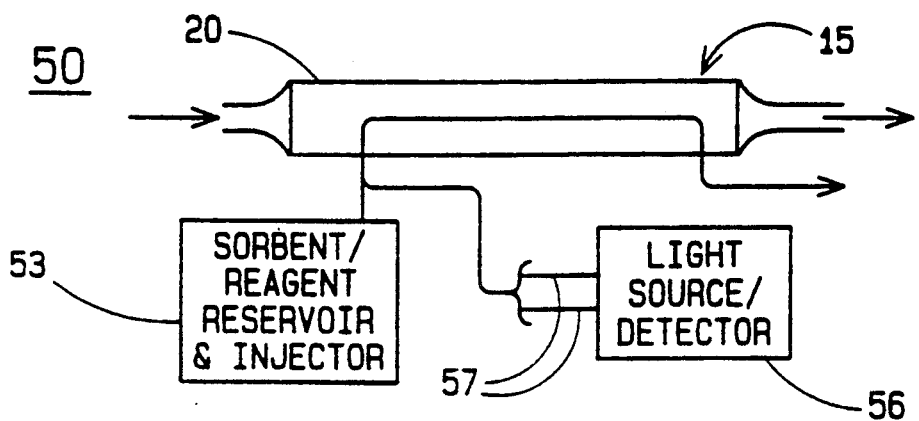
FIG. 5 is a functional block diagram of another embodiment of the present invention utilizing photometric detection with the use of optic fibers.

Referring now to FIG. 5, there is illustrated an analytical system 50, which is fundamentally similar to the system 40, but is even more readily adapted to portable applications. The system 50 includes the preconcentrator 15, which may be coupled to associated flow control devices as explained in connection with the system 40, but which have been omitted from FIG. 5 for simplicity. The system 50 also includes a sorbent/reagent reservoir and injector 53 which injects a combination of analyte-sorbing liquid and a suitable reagent tailored to the analyte of interest into the container 20 of the preconcentrator 15. There is also provided a light source/detector unit 56 which is coupled by optical fibers 57 to the container 20. More specifically, two optical fibers 57 may be respectively connected at one end thereof to the light source and to the light detector, while the other ends thereof are inserted in the container 20 at a distance sufficient to be disposed in use well within the preconcentrator 15.

In operation, the system 50 functions substantially the same as the system 40, described above, except that the analyte-enriched sorbing liquid is illuminated within the container 20, especially within the conical cavity 38, by one optic fiber, and any color change there can be detected and transmitted by the other optic fiber to the light source/detector unit 56. It will be appreciated that in this arrangement, the container 20 of the preconcentrator 15 need not be transparent or translucent.

Figure 6:
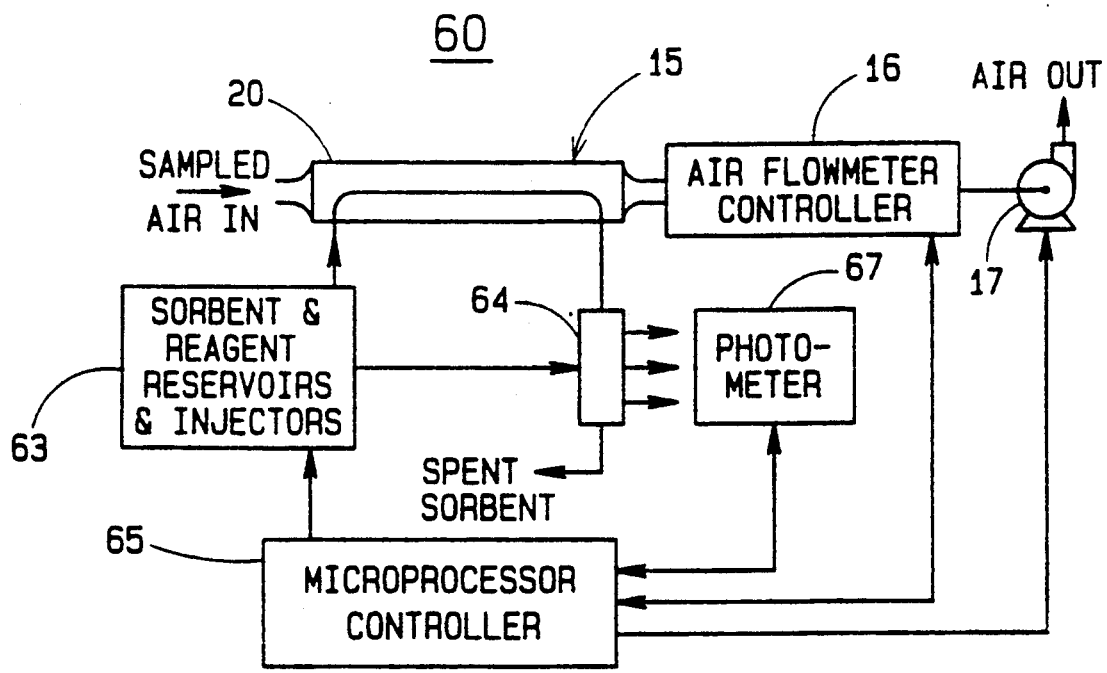
FIG. 6 is a functional block diagram of another embodiment of the invention utilizing chemiluminescence and photometric detection.

Referring now to FIG. 6, there is illustrated an analytical system 60 in accordance with the present invention, which utilizes chemiluminescent analyte detection. The system 60 includes the preconcentrator 15, the flowmeter controller 15 and the air pump 17 of the system 40, intercoupled and operating in the same manner described in connection with FIG. 4. The system 60 also includes sorbent and reagent reservoirs and injectors 63 coupled to the liquid input of the container 20 of the preconcentrator 15, the output of which is coupled to a transparent or translucent collection vessel 64. A microprocessor controller 65 is coupled to the sorbent and reagent reservoirs and injectors 63, the flowmeter 15 and the pump 17 in substantially the same manner as was described above in connection with the system 40. The system 60 also includes a photometer 67, which is coupled to the microprocessor controller 65.

The system 60 operates similarly to the system 40, except that the reagent injected into the container 20 is a chemiluminescence-generating reagent, rather than a color-generating reagent. When the analyte-enriched sorbing material is displaced into the collection vessel 64, the reaction of the analyte with the reagent produces a chemiluminescence which is detected by the photometer 67. The reservoirs and injectors 63 may be directly coupled to the collection vessel 64 for flushing the sorbent and reagent therethrough following each measurement. To transfer the analyte-enriched sorbing liquid from the preconcentrator 15 to the collection vessel 64, the microprocessor controller 65 may operate as in the aforedescribed system 40.

It will be appreciated that the reservoirs and injectors 43, 53 or 63 may be adapted to inject multiple different combinations of sorbents and reagents for detecting different analytes of interest. Thus, different combinations may be injected in successive sampling intervals, if desired, for detecting different analytes in the gaseous medium.

Figure 7:
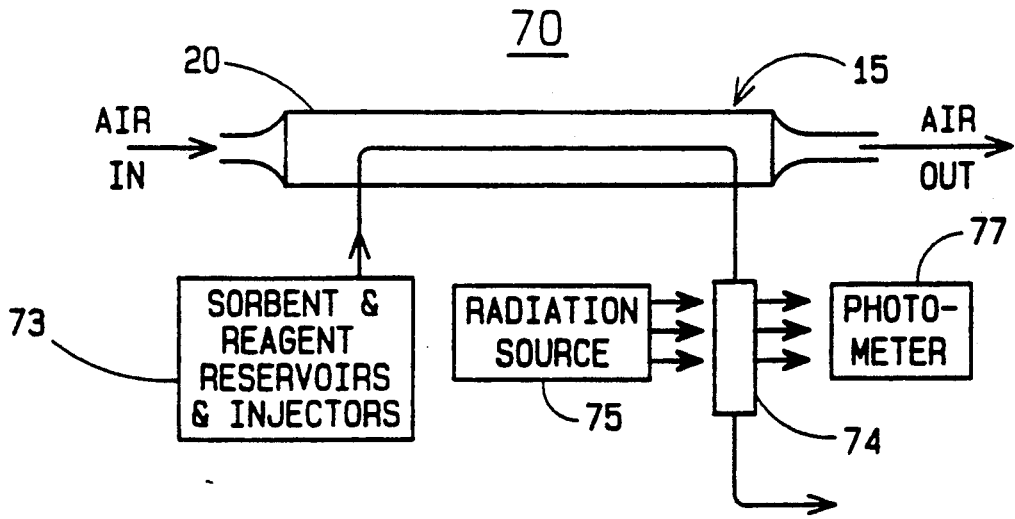
FIG. 7 is a functional block diagram of another embodiment of the invention utilizing fluorescence and photometric detection.

FIG. 7 depicts another photometric analytic system 70 which utilizes fluorescent detection of the analyte. The system 70 includes the preconcentrator 15 which may be coupled to the associated flow control devices for operation in substantially the same manner described above with respect to FIG. 6, but which have been omitted from FIG. 7 for simplicity. The system 70 includes sorbent and reagent reservoirs and injectors 73, which function substantially the same as the reservoirs and injectors 63 described above in connection with FIG. 6, except that the reagent injected is a fluorescence-generating reagent. The analyte-enriched sorbing liquid from the preconcentrator 15 is fed to a transparent or translucent collection vessel 74 which is illuminated by a radiation source 75, which emits a radiation of a type suitable for causing the product of the analyte/reagent reaction to fluoresce. The light emitted is detected by a photometer 77.

Figure 8:
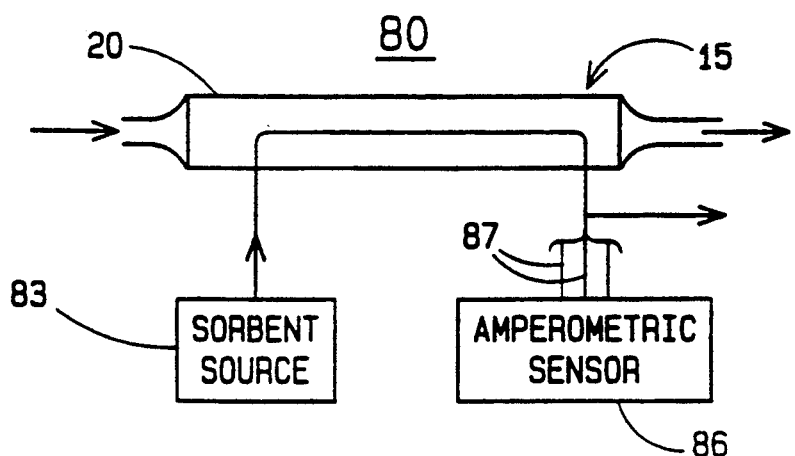
FIG. 8 is a functional block diagram of another embodiment of the invention utilizing amperometric detection.

In FIG. 8, there is illustrated an analytical system 80 in accordance with the present invention which utilizes amperometric sensing of the analyte. The system 80 is similar to the system 50, described above, and includes a preconcentrator 15 and a sorbent source 83 which is coupled to the liquid inlet of the container 20 of the preconcentrator 15 for introducing thereinto an analyte sorbing liquid designed to preferentially absorb the analyte of interest. There is also provided an amperometric sensor 86 having plural electrodes 87, which may be microelectrodes, and which are inserted into the container 20 of the preconcentrator 15 preferably within the conical cavity 38. It will be appreciated that the preconcentrator 15 may be coupled to associated flow control equipment, as was described above with respect to FIGS. 4 and 11, but which is omitted from FIG. 8 for simplicity. The electrodes 87 typically include a reference electrode, a counter electrode and a working or sensing electrode, to the latter of which a predetermined potential is applied, the presence of the analyte of interest generating a current signal which provides an indication of the presence of the analyte, in a well known manner.

Figure 9:
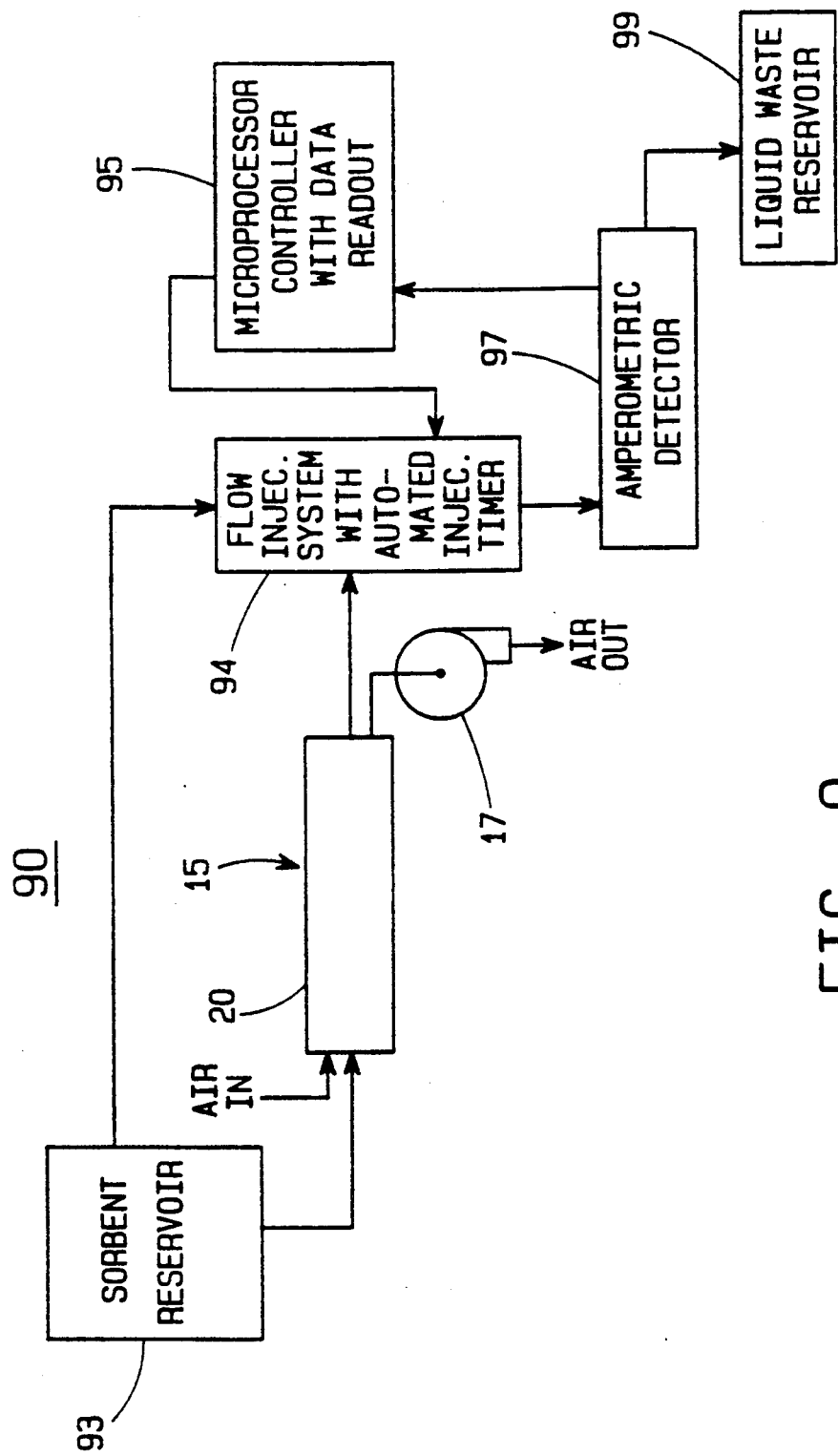
FIG. 9 is a functional block diagram of a still further embodiment of the invention utilizing amperometric detection.

In FIG. 9 there is illustrated an analytical system 90, which is a more detailed arrangement of the amperometric system 80. The system 90 includes the preconcentrator 15, the air outlet of which is coupled to the pump 17. The liquid inlet of the container 20 of the preconcentrator 15 is coupled to a sorbent reservoir 93, and its outlet is coupled to a flow injection system 94 which includes an automated injection timer, which is also coupled directly to the sorbent reservoir 93. A microprocessor controller 95 with data readout has an output coupled to the flow injection system 94. Analyte-enriched sorbing liquid is passed from the flow injection system 94 to an amperometric detector 97, which generates an output signal in response to the presence of the analyte of interest, which signal is coupled to the microprocessor controller 95. After passing through the amperometric detector 97 the sorbing liquid passes to a liquid waste reservoir 99. Alternatively, in the absence of an analyte signal, the liquid exiting from detector 97 may be recirculated to reservoir 93.

In operation, analyte-sorbing liquid is injected from the sorbent reservoir 93 into the container 20 of the preconcentrator 90, where it absorbs the analyte of interest from the sampled air. When a sufficient amount of the analyte has been absorbed, the analyte-enriched sorbing liquid is withdrawn from the conical cavity 38 of the preconcentrator 15 and passed to the flow injection system 94, which in turn injects it into the amperometric detector 97 for detection. The sensitivity of the detector 97 may be affected by the flow therethrough. Accordingly, the sorbent reservoir 93 is directly connected to the flow injection system 94 for flowing the sorbing liquid continuously through the detector 97. Then, when it is desired to sense the preconcentrated analyte, which is typically after a predetermined time period, an automatic timer in the flow injection system 94 switches the flow to shut off the flow from the sorbent reservoir 93 and permit flow from the preconcentrator 15. After the desired volume of sorbing liquid has been passed to the detector 97, the timer again switches to shut off the flow from the preconcentrator 15. The microprocessor controller 95 is responsive to the output signal form the detector 97 for varying the time periods set by the timer in the flow injection system 94. Thus, if the output signal is too low, the timer period between sample injections is increased, and it is decreased if the output signal is too high.

The amperometric systems of FIGS. 8-9 may be useful for the detection of chemically active compounds, such as hydrazine, methyl hydrazine and dimethyl hydrazine.

Of course, the afore-disclosed photometric or amperometric detectors may be replaced by other sensitive and selective sensing systems, such as those based on piezoelectric and/or immunoassay principles.

Figure 10:
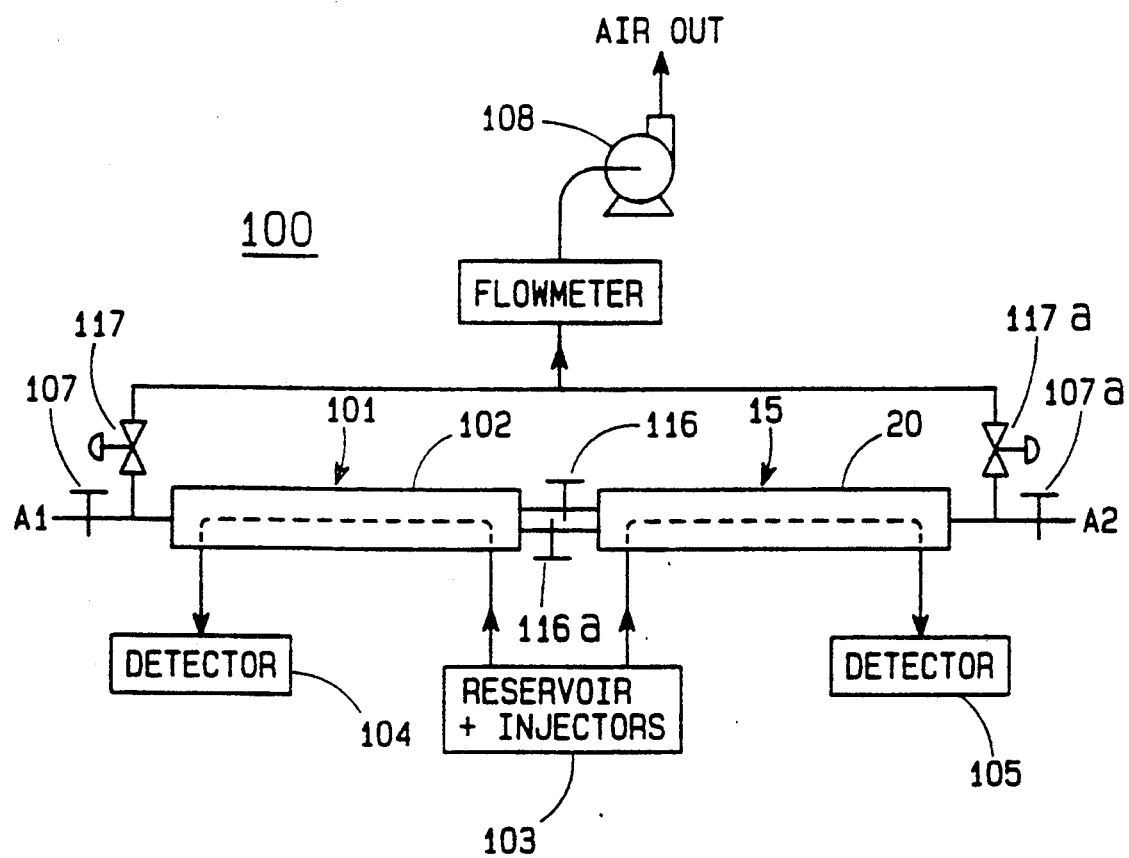
FIGS. 10a and 10b are functional block diagrams of calibration techniques for the analytical systems of the present invention.

FIG. 10 illustrates a technique for calibrating the preconcentrator of the present invention. The technique utilizes a calibration system 100, which includes a preconcentrator 101 having an elongated container 102 substantially identical to the preconcentrator means 15, coupled in series with the elongated container 20 of the preconcentrator means 15. A calibration injection means 103 introduces analyte-sorbing material continuously into the containers of each of the preconcentrator and calibration absorber. Two calibration detectors 104 and 105, respectively coupled to the containers 102 and 20, are responsive to analyte absorbed in the sorbing material, and respectively produce first and second output signals. Calibration flow means 106 includes valve means 107, 107a, 116, 116a, 117, and 117a, coupled for controlling the direction of flow of gaseous medium through the two series-connected containers 102 and 20, so as to permit a gaseous medium to be passed therethrough first in one direction, and then in the opposite direction.

Figure 10B:
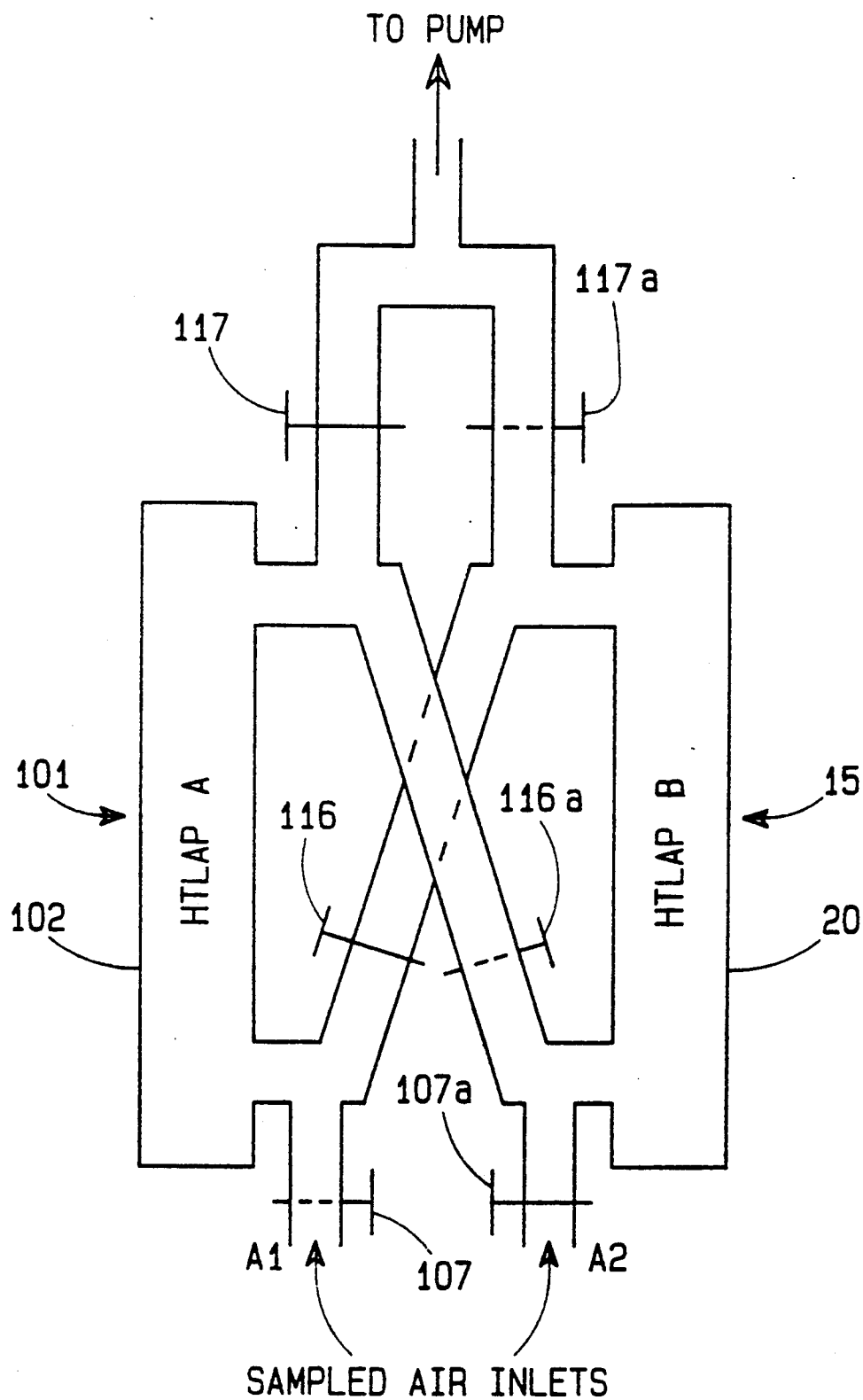

Essentially, the calibration technique comprises passing the sample gas through the series-connected preconcentrators 15 and 101, first in one direction and then in the other, and noting the readings of the detectors 104 and 105. More specifically, first the valves 107a, 116, and 117 are closed and the valves 107, 116a, and 117a are opened, and the sample medium is drawn through the preconcentrators 101 and 15 from left to right, as viewed in FIG. 10b, by the pump 108, and the readings on the detectors 104 and 105 are noted. These readings will presumably be different, since some of the analyte has been removed from the sample in the preconcentrator 101 and, therefore, the concentration should be less in the preconcentrator 15. Then, valves 107, 116a, and 117a are closed and valves 107a, 116, and 117 are opened, and the identical sample medium is drawn through the system in the opposite direction and the readings of the detectors 104 and 105 are again noted. The collection efficiencies $E_1$ and $E_2$ of the preconcentrators 104 and 105, respectively, are then related by the formulas:

$$E_1 = [c_{1f}c_{2r} - c_{1r}c_{2f}]/[c_{2r}(c_{1f} + c_{2f})]$$

and $$E_2 = [c_{1f}c_{2r} - c_{1r}c_{2f}]/[c_{1f}(c_{1r} + c_{2r})]$$

where $c_{1f}$ and $c_{2f}$ are, respectively, the readings of the detectors 104 and 105 during the first pass, the $c_{1r}$ and $c_{2r}$ are, respectively, the readings of the detectors 104 and 105 during the second or reverse pass. These formulas are valid only if equal volumes of air are passed in both directions and if the volumes of liquid sorbent in preconcentrators 15 and 101 are the same.

Of course, the components of FIG. 10 can be interfaced with a microprocessor controller (not shown) so that the calibration could be automatically performed at programmed intervals.

A method in accordance with the invention for preconcentrating traces of an analyte in a gaseous medium, such as air, includes providing a length of wettable material within the container 20, continuously wetting the wettable material of the container 20 with an analyte-sorbing liquid so that the liquid moves slowly toward one end of the wettable material for wetting virtually the entire length. Air flows through the inlet opening 31, over the length of the material for trapping and preconcentrating traces of the analyte in the sorbing liquid. The liquid is then collected from the one end of the wettable material.

Aerosol collection is also a highly effective preconcentration method that enhances the detection capabilities of the HTLAP-analyzer system. Since the centrifugal air motions in the HTLAP favor the transfer of a substantial portion of entrained aerosols into the liquid extractant, the device can also collect traces of nonvolatile analytes, such as cocaine or heroin, from aerosols as well as from the vapor phase. Thus, the method aspect also may include extracting the analyte from aerosol particles collected by the sorbing liquid, and drawing the aerosol into the container 20. The aerosol may consist of fine liquid droplets or of fine solid particulates suspended in the gaseous medium.

Another variation of this method is to generate an aerosol, e.g., a fine mist or fog, which would preconcentrate traces of an analyte, drawing the aerosol through the preconcentrator, and extracting the analyte from the collected aerosol particles.

In cases where the dust concentration in the sampled air is too low to yield a significant aerosol contribution, such as when suspected contents are well packaged in plastic material to which most dust particles will be electrostatically attracted, the most effective way of collecting any adhering particles or of extracting any analytes that may be adsorbed onto solid surfaces is to swipe the inner walls of containers (i.e. boxes, luggage, or crates) with a sponge or swab containing a liquid extractant, and to inject the collected extractant into a highly sensitive analyzer.

From the foregoing, it can be seen that there has been provided a simple, fast-acting and inexpensive analytical system for preconcentrating and detecting trace levels of analytes, such as hazardous materials, and which is uniquely adapted for use in portable devices, particularly automated or semi-automated devices for rapid on-site detection and quantification of such analytes. The system is adapted for use with multiple detection techniques, including photometric and amperometric techniques, while providing greater sensitivity, wider measurable concentration range and greater flexibility than prior devices using such techniques.

The embodiments of the invention in which an exclusive property or privilege is claimed are defined as follows:

I claim:

1. A method for preconcentrating an analyte in a gaseous medium comprising the steps of:

providing a length of wettable material within an inner wall surface of a container, wetting one part of the wettable material with an analyte-sorbing liquid so that the liquid moves toward one end of the wettable material for wetting substantially the length thereof, flowing the gaseous medium through an inlet opening into the container, over the liquid that is wetting said material in direct contact therewith for trapping and preconcentrating traces of analyte in the sorbing liquid, and collecting from the one end of the wettable material the sorbing liquid containing the preconcentrated traces of analyte, limiting any dry surfaces within or connected to said container that the gaseous medium may encounter before contacting the liquid to a negligibly small area, or maintaining the dry surfaces at a temperature at which adsorption of the analyte is negligibly low, and detecting said analyte, preconcentrated within said sorbing liquid by an analyte detection means, producing a signal indicative of the presence of said analyte, wherein the volume of sorbing liquid is reduced by allowing the liquid to collect within a portion of the container and to partially evaporate.

2. A method for preconcentrating an analyte in a gaseous medium comprising the steps of:

providing a length of wettable material within an inner wall surface of a container, wetting one part of the wettable material with an analyte-sorbing liquid so that the liquid moves toward one end of the wettable material for wetting substantially the length thereof, flowing the gaseous medium through an inlet opening into the container, over the liquid that is wetting said material in direct contact therewith for trapping and preconcentrating traces of analyte in the sorbing liquid, and collecting from the one end of the wettable material the sorbing liquid containing the preconcentrated traces of analyte, limiting any dry surfaces within or connected to said container that the gaseous medium may encounter before contacting the liquid to a negligibly small area, or maintaining the dry surfaces at a temperature at which adsorption of the analyte is negligibly low, and detecting said analyte, preconcentrated within said sorbing liquid by an analyte detection means, producing a signal indicative of the presence of said analyte, wherein said temperature is at least 50° C.

3. A method of collecting liquid or solid particulates from a gaseous medium comprising the steps of:

providing a cylindrical container with a cylindrical wettable interior wall surface, substantially wetting said interior wall surface with a liquid film that is moving toward one end of said container, flowing the gaseous medium through an inlet opening into the container over the wetted interior wall surface so that a significant fraction of particulates from the gaseous medium is transferred into the liquid film, collecting from the one end of the container a liquid sample that is enriched in said particulates, and, detecting said particulates, collected within said liquid sample by a detection means, producing a signal indicative of the presence of said particulates, wherein the volume of the liquid sample is reduced by allowing the liquid sample to collect at the end of the container and to partially evaporate.

4. The method of claim 3, comprising the preliminary steps of preconcentrating traces of an analyte in an aerosol, the aerosol consisting of fine liquid droplets or of fine solid particulates suspended in the gaseous medium, and drawing the aerosol into the container.

5. A method of collecting an analyte from a gaseous medium comprising the steps of:

providing a cylindrical container with a cylindrical wettable interior wall surface, wetting said interior wall surface with a liquid film that is moving toward one end of said container, flowing the gaseous medium through an inlet opening into the container over the wetted interior wall surface in a swirling and highly turbulent motion, so that a significant fraction of the analyte from the gaseous medium is transferred into the liquid film, and withdrawing from the one end of the container a liquid sample that is enriched in said analyte, and detecting said analyte within said liquid sample by an analyte detection means, producing a signal indicative of the presence of said analyte, wherein the volume of the liquid sample is reduced by allowing the liquid sample to collect within a portion of the container and to partially evaporate.

6. The method of claim 5, wherein the flow of said gaseous medium is directed away from said container end.

7. The method of claim 5, which includes the step of exposing at least part of said liquid sample to said analyte detection means at an appropriate rate.

8. The method of claim 7, which includes the step of inserting said detection means within said container.

9. The method of claim 7, which includes the step of feeding said liquid sample to said detection means.

10. The method of claim 7, which includes causing said detection means to transmit electrical optical signals to a control means that, in turn, causes the rate or frequency of sample withdrawals from said container end to be adjusted in accordance with said signals.

11. The method of claim 7, wherein said detection means utilizes a photometric, electrochemical, piezoelectric or immunoassay technique.

12. The method of claim 11, wherein said photometric technique is based on a change of color, light absorptivity, chemiluminescence or fluorescence arising from the presence of the analyte.

13. The method of claim 11, wherein said electrochemical technique uses amperometric detection.

14. The method of claim 7, wherein said detection means includes an optical fiber or a miniaturized electrode.

15. The method of claim 5, which includes retaining the liquid sample within the container for the duration of a sampling period prior to withdrawing it from said container end.

16. The method of claim 5, wherein said liquid sample is continuously withdrawn from said container end.

17. The method of claim 5, wherein said liquid medium comprises a soap, detergent or other wetting agent.

18. The method of claim 17, wherein said wetting agent is an ionizable or otherwise polar long-chain hydrocarbon compound.

19. The method of claim 7, wherein said liquid medium comprises a substance that reacts with said analyte to yield a compound that is detected by said detection means.

* * * * *